US008623335B2

(12) United States Patent
Waddington

(10) Patent No.: US 8,623,335 B2
(45) Date of Patent: Jan. 7, 2014

(54) SCAR AND ROSACEA AND OTHER SKIN CARE TREATMENT COMPOSITION AND METHOD

(76) Inventor: Tauna Ann Waddington, Clifton Park, NY (US)

( * ) Notice: Subject to any disclaimer, the term of this patent is extended or adjusted under 35 U.S.C. 154(b) by 1050 days.

(21) Appl. No.: 12/206,833

(22) Filed: Sep. 9, 2008

(65) Prior Publication Data

US 2009/0068128 A1 Mar. 12, 2009

Related U.S. Application Data

(60) Provisional application No. 60/971,025, filed on Sep. 10, 2007.

(51) Int. Cl.
*A61K 8/92* (2006.01)
*A61K 8/97* (2006.01)
*A61Q 17/04* (2006.01)
*A61Q 19/00* (2006.01)
*A61K 38/19* (2006.01)

(52) U.S. Cl.
USPC ............ 424/59; 424/744; 424/639; 424/85.1; 514/2; 514/559

(58) Field of Classification Search
USPC ................ 424/59, 744, 639, 85.1; 514/2, 559
See application file for complete search history.

(56) References Cited

U.S. PATENT DOCUMENTS

| 6,214,352 B1 | 4/2001 | Matsukawa |
| 6,294,179 B1 * | 9/2001 | Lee et al. ...................... 424/401 |
| 6,342,208 B1 | 1/2002 | Hyldgaard et al. |
| 6,348,200 B1 | 2/2002 | Nakajima et al. |
| 6,419,962 B1 | 7/2002 | Yokoyama et al. |
| 6,579,543 B1 | 6/2003 | McClung |
| 6,932,975 B2 | 8/2005 | Ishikawa et al. |
| 2002/0106337 A1 * | 8/2002 | Deckers et al. .................. 424/59 |
| 2004/0076654 A1 * | 4/2004 | Vinson et al. .................. 424/401 |
| 2005/0208150 A1 * | 9/2005 | Mitts et al. ..................... 424/639 |
| 2005/0266064 A1 | 12/2005 | McCarthy |

FOREIGN PATENT DOCUMENTS

CN        1295800 A  *  5/2001  .............. A23L 1/076

OTHER PUBLICATIONS

Dillard et al. "Alternative Medicine for Dummies", IDG Book Worldwide, Foster City, CA; 1998.*
RECARE 888808 reVitalize (Clarifies, Firms & Brightens Skin). [online] 3 pages. (Product information page) [retrieved on Sep. 8, 2008]. Retrieved on the internet:< URL: http://www.carebizint.com/int-en/recare.html>.
Dr. Hauschka Rhythmic Night Conditioner. [online]. 2 pages. (Product information page) lilou-organics.com. [retrieved Sep. 8, 2008]. Retrieved from the internet:< URL: http://www.lilou-organics.com/scripts/prodView_products.asp?idproduct=37>.

* cited by examiner

*Primary Examiner* — Ernst Arnold
*Assistant Examiner* — Hong Yu
(74) *Attorney, Agent, or Firm* — Schmeiser, Olsen & Watts, LLP

(57) ABSTRACT

The present invention relates generally to composition and methods for topical application to skin. More particularly, it relates to treatment of scars and rosacea, and other aspects of skin care. A composition is disclosed having a skin toner for cleansing a skin surface, removing dead skin cells, restoring alkali balance, and shrinking skin pores; and a skin moisturizer for increasing water content in the external layers of the skin.

19 Claims, No Drawings

SCAR AND ROSACEA AND OTHER SKIN CARE TREATMENT COMPOSITION AND METHOD

BACKGROUND OF THE INVENTION

1. Technical Field

The present invention relates generally to composition and methods for topical application to skin. More particularly, it relates to treatment of scars and rosacea, and other aspects of skin care.

2. Related Art

Conventional scar treatment does not adequately provide for other aspects of skin care. Conventional scar treatments are designed for application only to a local area containing a scar, not to skin generally. Often, the chemicals used in scar treatment products are not as desirable for use elsewhere on unscarred skin. This can result in unnecessary effort, expense, and complication when using various scar and skin care products to treat a scar and also care for the skin generally in surrounding areas.

The present invention overcomes these disadvantages by combining nourishing, natural products that benefit and promote the health of skin generally, and are also effective for treatment of scars and rosacea. This removes the expense of additional skin care products which, in turn, eliminates the extra effort and complication associated with using the additional products.

SUMMARY OF THE INVENTION

The present invention relates generally to compositions for topical application to skin. More particularly, it relates to treatment of scars and rosacea, and other aspects of skin care.

In a first aspect, the present invention is a composition comprising: a skin toner for cleansing a skin surface, removing dead skin cells, restoring alkali balance, and shrinking skin pores; and a skin moisturizer for increasing water content in the external layers of the skin.

In a second aspect, the present invention is a composition comprising: a skin toner, wherein the skin toner comprises aloe, glycerin, vitamin E, royal jelly, and witch hazel; and a skin moisturizer, wherein the skin moisturizer comprises almond oil, avocado oil, coconut oil, emu oil, olive oil, and sesame oil.

In a third aspect, the present invention is A composition comprising: an almond oil present up to about 8% by volume; an aloe vera gel present in a range of between about 25% to about 40% by volume; an avocado oil present in a range of between about 5% to about 15% by volume; coconut oil present up to about 5% by volume; an emu oil present up to about 5% by volume; a vegetable glycerin present up to about 3% by volume; a royal jelly freeze dried in a 3.5× concentration present up to about 1% by volume; a sesame oil present in a range of between about 5% to about 15% by volume; a vitamin E present up to about 3% by volume; and a witch hazel extract present in a range of between about 25% to about 40% by volume.

In a fourth aspect, the present invention is a method of treating skin comprising: providing a skin treatment composition including almond oil, aloe, avocado oil, coconut oil, emu oil, glycerin, royal jelly, sesame oil, vitamin E, and witch hazel; supplying a skin surface with said skin treatment composition; and applying the skin treatment composition to the skin.

DETAILED DESCRIPTION OF THE INVENTION

Although certain embodiments of the present invention will be shown and described in detail, it should be understood that various changes and modifications may be made without departing from the scope of the appended claims. The scope of the present invention will in no way be limited to the number of constituting components, the materials thereof, the shapes thereof, the relative arrangement thereof, etc., and are disclosed simply as an example of an embodiment. The features and advantages of the present invention are illustrated in detail in the accompanying drawings, wherein like reference numerals refer to like elements throughout the drawings.

As a preface to the detailed description, it should be noted that, as used in this specification and the appended claims, the singular forms "a", "an" and "the" include plural referents, unless the context clearly dictates otherwise.

The composition of the present invention has been found to have superior and unexpected properties when applied to skin such as reducing redness associated with scars and rosacea, and also flattening raised scars. The composition may include ingredients that serve two general functions: toning and moisturizing skin. Skin toner may cleanse skin, remove dead skin cells, restore alkali balance, and shrink pores. Skin moisturizer may increase water content in the external layers of the skin.

Skin toner may be formulated in various strengths including skin bracers, fresheners, tonics, and astringents. A skin toner may be comprised of a single skin toning ingredient such as witch hazel or it may be comprised of a plurality of ingredients which may be included to serve diverse purposes such as humectants and antiseptics. Water may also be among the ingredients included in a skin toner.

Skin toner may include alum, oatmeal, witch hazel, rubbing alcohol, silver nitrate, zinc oxide, zinc sulfate, Burow's solution, tincture of benzoin, tannic acid, gallic acid, aluminum citrate, aluminum lactate, birch extract, coffee extract, evening primrose extract, grape extract, henna extract, ivy extract, lemon extract, aluminum salts, alfalfa extract, betula extract, citrus extract, dandelion extract, golden seal extract, honeysuckle extract, hops extract, ivy extract, lemon extract, plantain extract, sambucus canadensis extract, tea tree oil, thyme extract, or any other skin toner.

Moisturizers may impart or restore moisture to skin. Increasing skin water content may make the skin softer and more pliable. Moisturizers may serve to mimic the action of normal skin secretions in maintaining suppleness in the skin and provide a barrier to evaporation. Skin moisturizer may include two general types: occlusives and humectants. Occlusive moisturizers form a layer on the skin which reduces the rate of evaporation. Humectants are nonocclusive hygroscopic substances which retain water and make the water available to the skin. Humectants may also function by improving the lubricity of the skin. Both occlusive and humectant moisturizers may be suitable for use in the present invention. A moisturizer may be comprised of a single moisturizing ingredient such as glycerin or it may be comprised of a plurality of ingredients which may be included to serve diverse purposes such as emollients, emulsifiers, lipids, surfactants, thickeners, and preservatives. Further, a moisturizer may have both occlusive and nonocclusive properties. Water may be among the ingredients included in a moisturizer. Selection of the levels and types of moisturizers incorporated in the composition may be made without adversely affecting the stability of the composition or its in-use characteristics.

A moisturizer may include long chain $C_{12}$-$C_{22}$ fatty acids, liquid water-soluble polyols, glycerin, propylene glycol, sorbitol, polyethylene glycol, ethoxylated/propoxylated ethers of methyl glucose, ethoxylated/propoxylated ethers of lanolin alcohol, lanolin alcohol, coconut fatty acid, tallow fatty acid, nonocclusive liquid water-soluble polyols, aloe vera gel, aloe vera gel condensed, aloe vera gel freeze-dried powder, aloe vera gel oil extract, amino acids, amniotic fluid, avocadin, calcium protein complex, cashew oil, chia oil, chitin, chitosan, chitosan PCA, cholesteric esters, chondroitin sulfate, collagen, collagen amino acids, copper protein complex, dioctyl maleate, dipentaerythritol fatty acid ester, elastin, ethyl panthenol, evening primrose oil, glycereth-12, glycosphingo lipids, honey, hyaluronic acid, hybrid safflower oil, hydrogenated polyisobutene, hydrolyzed collagen, hydrolyzed elastin, hydrolyzed fibronectin, hydrolyzed mucopolysaccharides, hydrolyzed silk, hydrolyzed wheat protein, jojoba esters, keratin amino acids, kiwi fruit extract, lactamide MEA, liposomes, live yeast cell derivative liposome, marina polyaminosaccharide, mineral oil, mink oil ethyl ether, mucopolysaccharides, mucopolysaccharides, palmetto extract, pantethine, paraffin, PEG-4, PEG-6, PEG-8, PEG-12, PEG-100 stearate, perfluoropolymethyl-isopropyl ether, petrolatum, petroleum wax, pistachio oil, placenta extract, plankton extract, polyamino sugar condensate, polybutene, polyglyceryl methacrylate, polypentaerythrityl tetralaurate, PPG-10 butanediol, PPG-20 methyl glucose ether distearate, royal jelly extract, saccharide isomerate, selenium protein complex, serum albumin, sodium hyaluronate dimethylsilanol, sodium lactate methylsilonol, sodium mannuronate methylsilanol, soluble collagen, super oxide dismutase, super oxide dismutase liposome, tissue extract, tocopheryl linoleate, lipophylic moisturizers such as lysolecithin, lecithin, cholesterol, cholesterol esters, sphingolipids, or ceramides, low molecular moisturizer such as serine, glutamine, sorbitol, mannitol, glycerin, sodium pyrrolidone-carboxylate, 1,3-butylene glycol, propylene glycol, lactic acid, or lactic acid salts, high molecular moisturizers such as hyaluronic acid, sodium hyaluronate, elastin, alginic acid, mucopolysaccharides, polyethylene glycol, polyaspartic acid salts, or water soluble chitin, hydrocarbon oils, hydrocarbon waxes, silicones, fatty acid derivatives, cholesterol, cholesterol derivatives, di- and tri-glycerides, vegetable oils, vegetable oil derivatives, liquid nondigestible oils, blends of liquid digestible or nondigestible oils with solid polyol polyesters, acetoglyceride esters, alkyl esters, alkenyl esters, lanolin and its derivatives, milk tri-glycerides, wax esters, beeswax derivatives, sterols, phospholipids, or any other moisturizer ingredient.

An occlusive moisturizer may be petrolatum, paraffin, waxes, greases, mineral oil, beeswax, lanolin and oil-soluble lanolin derivatives, saturated and unsaturated fatty alcohols such as behenyl alcohol, squalene, various animal and vegetable oils such as almond oil, apricot oil, apricot pit oil, avocado oil, cade oil, castor oil, cinnamon oil, corn oil, cottonseed oil, evening primrose oil, grape oil, grape seed oil, hazelnut oil, jojoba oil, linseed oil, liver oil, macadamia nut oil, mink oil, neetsfoot oil, olive oil, palm kernel oil, palm nut oil, palm oil, peach pit oil, peanut oil, pine oil, pistachio nut oil, poppyseed oil, rapeseed oil, rice bran oil, rice germ oil, safflower oil, sasanqua oil, sesame oil, sesame seed oil, soybean oil, sunflower oil, sunflower seed oil, tsubaki oil, walnut oil, wheat germ oil, wheat germ oil, teaseed oil, triglycerine, glycerine trioctanate, glycerine triisopalmitate, cacao fat, beef tallow, sheep fat, hog fat, horse fat, hydrogenated oil, hydrogenated castor oil, Japanese wax, shea butter, beeswax, candelilla wax, cotton wax, carnauba wax, bayberry wax, tree wax, spermaceti, montan wax, bran wax, lanolin, reduced lanolin, hard lanolin, kapok wax, sugarcane wax, jojoba wax, shellac wax, or any other moisturizer exhibiting occlusive properties.

A humectant may be glycerin, sorbitol, urea, alpha hydroxy acids, sugars, lactic acid, propylene glycol, glyceryl triacetate, lithium chloride, polyols like sorbitol, xylitol and maltitol, polymeric polyols like polydextrose, natural extracts like quillaia, hexadecyl, myristyl, isodecyl and isopropyl esters of adipic, lactic, oleic, stearic, isostearic, myristic and linoleic acids, as well as many of their corresponding alcohol esters (e.g., sodium isostearoyl-2-lactylate, sodium capryl lactylate), hydrolyzed protein and other collagen-derived proteins, aloe vera gel, acetamide MEA (acetmonoethanolamide), compounds found to be naturally occurring in the stratum corneum of the skin such as sodium pyrrolidone carboxylic acid, lactic acid, urea, L-proline, guanidine and pyrrolidone, acetamide MEA, acetamido propyl trimonium chloride, calcium stearoyl lactylate, chitosan PCA, diglycerol lactate, ethyl ester of hydrolyzed silk, fatty quaternary amine chloride complex, glycereth-7, glycereth-12, glycereth-26, glycereth-4.5 lactate, glycerin, diglycerin, polyglycerin, honey, hydrolyzed fibronectin, lactamide MEA, lactamide N-(2-hydroxyetheryl), mannitol, methyl gluceth-10, methyl gluceth-20, methylsilanol PCA, panthenol, PCA, PEG-4, PEG-8, polyamino sugar condensate, quaternium-22, sea salts, sodium capryllactylate, sodium hyaluronate, sodium isostearoyl lactylate, sodium lactate, sodiumlauroyl lactylate, sodium PCA, sodium polyglutamate, sodium stearoyl lactylate, soluble collagen, sorbitan laurate, sorbitan oleate, sorbitan sesquiisostearate, sorbitan stearate, sorbitol, sphingolipids, TEA-PCA, ethylene glycol, diethylene glycol, triethylene glycol, and other polyethylene glycols, propylene glycol, dipropylene glycol and other propylene glycols, 1,3-butylene glycol, 1,4-butylene glycol and other butylene glycols, glycerol, diglycerol and other polyglycerols, mannitol, xylitol, maltitol and other sugar alcohols, glycerol ethylene oxide (EO) and propylene oxide (PO) adducts, sugar alcohol EO and PO adducts, adducts of EO or PO and monosaccharides such as galactose and fructose, adducts of EO or PO and polysaccharides such as maltose and lactose, sodium pyrrolidonecarboxylate, polyoxyethylene methyl glycoside, polyethylene glycol, propylene glycol, dipropylene glycol, 1,3-butylene glycol, hexylene glycol, xylitol, maltitol, maltose, D-mannitol, gluten, glucose, fructose, lactose, sodium chondroitin sulfate, sodium hyalonate, sodium adenosine phosphate, gallates, pyrrolidone carbonates, glucosamine, cyclodextrin, alpha hydroxy acids, 2-methyl-1,3-propane diol, or any other moisturizer exhibiting humectant properties.

A moisturizer may include agents that mimic natural ingredients and function as botanicals, including vitamins, hydroxy acids, and retinoids. Vitamins may include vitamin A, retinol, retinol palmitate, inositol, pyridoxine chlorate, benzyl nicotinate, nicotinamide, dl$\alpha$-tocopheryl nicotine, magnesium ascorbyl phosphate, vitamin $D_2$ (ergocalciferol), dl$\alpha$-tocopherol, potassium dl-$\alpha$-tocopherol-2-L-ascorbic diester, dl-$\alpha$-tocopheryl acetate, pantothenic acid, biotin, or any other vitamin. Some ingredients that may reduce the severity of dry skin are alpha hydroxy acids (AHA) and beta hydroxy acids (BHA), including their salts, as well as retinoids. The hydroxy acids are classified according to the number of carboxylic acids on their configuration. Monocarboxylic acids are glycolic, lactic, and mandelic acids. Dicarboxylic acids include malic and tartaric acids. Tricarboxylic acids embody citric acid found in citrus fruits. The BHAs encompass mostly salicylic acid and its derivatives. AHAs have been shown to exfoliate. Thus, they are useful in hyperkeratotic conditions. They act as humectants and have a normalizing effect on the stratum corneum, increasing its plasticity and flexibility. Other ingredients of a moisturizer may include elastin, lecithin, sodium hyaluronate, sodium passive cutaneous anaphylaxis, ceramides, naturally occurring skin lipids and sterols, artificial or natural oils, humectants, emollients, emulsifiers, preservatives, lubricants, greases, natural moisturizing factors (NMF) including low molecular weight substances such as ammonia, amino acids, glucosamine, creatinine, citrate and ionic solutions such as sodium, potassium, chloride, phosphate, calcium and magnesium, sodium pyrrolidone carboxylic acid, hexadecyl, myristyl, isodecyl, or isopropyl esters of adipic, lactic, oleic, stearic, isostearic, myristic and linoleic acids, and their corresponding alcohol esters, sodium isostearoyl-2-lactylate and sodium capryl lactylate, glycerin, polyethylene glycol, propylene glycol, sorbitol, polyethylene glycol and propylene glycol ethers of methyl glucose, polyethylene glycol and propylene glycol ethers of lanolin alcohol, lactic acid, L-proline, and other free fatty acids, coconut fatty acid, tallow fatty acid, nonocclusive liquid water-soluble polyols and the essential amino acid compounds found naturally in the skin, and stearic and lauric acids.

Emollients may smooth roughened skin, change the skin's appearance, lubricate, replace natural skin lipids, and provide occlusion. Emollients may be composed of water in oil emulsions. An emollient may make something soft or supple, and may also sooth the skin or mucous membrane. Emollients, such as lanolin, shea butter, or petrolatum may act as a barrier (occlusion effect) against loss of water and also as a softener of stratum corneum. Other emollients may be oil-water emulsions of varying composition and may include several esters and oils such as octyl dodecanol, hexyl decanol, oleyl alcohol, decyl oleate, isopropyl stearate, isopropyl palmitate, isopropyl myristate, hexyl laureate, and dioctyl cyclohexane. Further, emollients may include long-chain acylglutamic acid cholesteryl esters, cholesteryl hydroxystearate, 12-hydroxystearic acid, stearic acid, rhodinic acid, lanolin fatty acid cholesteryl ester, petrolatum, cocoa butter, esters of fatty acids, glycerin mono-, di-, and tri-esters, epidermal and sebaceous hydrocarbons such as cholesterol, cholesterol esters, squalane, silicone oils and gums, mineral oil, lanolin and derivatives, castor oil, almond oil, oleyl oleate, or any other emollient ingredient.

An emulsifier may be a substance that is capable of lowering the interfacial tension between an oil and an aqueous phase and, thus, may aid the dispersal of oil (in the case of oil-in-water emulsions) and water (in the case of water-in-oil emulsions), respectively, into droplets of a small size and help to maintain the particles in a dispersed state. Emulsifiers may be generally classified as i) proteins or carbohydrate polymers, which act by coating the surface of the dispersed fat or oil particles, thus preventing them from coalescing; such emulsifiers are sometimes also called protective colloids, and ii) long-chain alcohols and fatty acids, which are able to reduce the surface tension at the interface of the suspended particles because of the solubility properties of their molecules. Soaps behave in this manner when they exert cleaning action by emulsifying the oily components of soils.

The composition may include surfactants. Surfactants may be detergent, soap base, sodium laurate, sodium palmitate, or any other fatty acid soap, sodium laurosulfate, potassium laurosulfate, or any other higher alkyl sulfate ester salt, POE laurosulfate triethanol amine, sodium POE laurosulfate, or any other alkyl ester sulfate ester salt, sodium lauroylsarcosine or any other N-acylsarcosine acid, sodium N-myristyl-N-methyltaurine, sodium N-cocoyl-N-methyl taurate, sodium laurylmethyl taurate, or any other higher fatty acid amide sulfonate, sodium POE oleyl ether phosphate, POE stearyl ether phosphate, or any other phosphate ester salt, sodium di-2-ethylhexyl-sulfosuccinate, sodium monolauroylmonoethanol amide polyoxyethylene sulfosuccinate, sodium laurylpoly-propylene glycol sulfosuccinate, or any other sulfosuccinate, linear sodium dedecylbenzensulfonate, linear dodecylbenzensulfonate triethanol amine, linear dodecyl benzensulfate, or any other alkylbenzensulfonate, sodium N-lauroylglutamate, disodium N-stearoylglutamate, monosodium N-myristoyl-L-glutamate, or any other N-acylglutamate, sodium hydrogenated castor oil fatty acid glycine sulfate or any other higher fatty acid ester sulfate ester salt, Turkey red oil or any other sulfated oil, POE alkyl ether carboxylic acid, POE alkylaryl ether carboxylate, α-olefinsulfates, higher fatty acid ester sulfonates, secondary alcohol sulfate ester salts, higher fatty acid alkylolamide sulfate ester salts, sodium lauroyl monoethanolamide succinate, N-palmitoyl asparaginate ditriethanol amine, sodium caseine, or any other anionic surfactant, stearyl trimethyl ammonium chloride, lauryl trimethyl ammonium chloride, or any other alkyl trimethyl ammonium salt, distearyldimethyl ammonium chloride, dialkyldimethyl ammonium chloride salts, poly(N,N'-dimethyl-3,5-methylenepiperidinium)chloride, cetylpyridinium chloride or any other alkyl pyridinium salt, alkyl quaternary ammonium salts, alkyl dimethylbenzyl ammonium salts, alkyl isoquinolinium salts, dialkyl morphonium salts, POE alkyl amines, alkyl amine salts, polyamine fatty acid derivatives, amyl alcohol fatty acid derivatives, benzalkonium chloride, benzethonium chloride, or any other cationic surfactant, sodium 2-undecyl-N,N,N-(hydroxyethylcarboxymethyl)-2-imidazoline, 2-cocoyl-2-imidazoliniumhydroxide-1-carboxyethyloxy-2-sodium salt, or any other imidazoline family bipolar surfactant, 2-heptadecyl-N-carboxymethyl-N-hydroxyethylimidazolinium betaine, lauryldimethyl-aminoacetate betaine, alkyl betaine, amide betaine, sulfo betaine, or any other betaine family surfactant, or any other bipolar surfactant, sorbitan monooleate, sorbitan monoisostearate, sorbitan monolaurate, sorbitan monopalmitate, sorbitan monostearate, sorbitan sesquioleate, sorbitan trioleate, diglyceryl sorbitan pentaoctanoate, diglyceryl sorbitan tetraoctanoate, or any other sorbitan fatty acid ester, glycerin mono cotton seed oil fatty acid, glycerin monoerucate, glycerin sesquioleate, glycerin monostearate, glycerin α,α-oleate pyroglutamate, monostearate glycerin malic acid or any other glycerin or polyglycerin fatty acid, propylene glycol monostearate or any other propylene glycol fatty acid ester, hydrogenated castor oil derivatives, glycerin alkyl ethers, polyoxyethylene methylpolysiloxane copolymers, or any other lyophilic nonionic surfactant, POE sorbitan monooleate, PO-sorbitan monostearate, POE-sorbitan monooleate, POE-sorbitan tetraoleate, or any other POE sorbitan fatty acid ester, POE-sorbite monolaurate, POE-sorbitan monooleate, POE-sorbite pentaoleate, POE-sorbitan monostearate, or any other POE sorbitan fatty acid ester, POE-glycerin monostearate, POE-glycerin monoisostearate, POE-glycerin triisostearate, or any other POE glycerin fatty acid ester, POE monooleate, POE distearate, POE monodioleate, distearate ethylene glycol, or any other POE fatty acid ester, POE lauryl ethers, POE oleyl ethers, POE stearyl ethers, POE behenyl ethers, POE2-octyldodecyl ethers, POE cholestanol ethers, or any other POE alkyl ether, POE octyl phenyl ethers, POE nonyl phenyl ethers, POE dinonyl phenyl ethers, or any other POE alkyl phenyl ether, Pluronic or any other poloxamer, POE.POP cetyl ethers, POE.POP-2-decyltetradecyl ethers, POE.POP monobutyl ethers, POE.POP hydrated lanolin, POE.POP glycerin ethers, or any other POE-POP alkyl ether, Tetronic or any other tetra-POE.tetra-POP ethylene diamine condensation product, POE castor oil, POE hydrogenated castor oil, POE hydrogenated castor oil monoisostearate, POE hydrogenated castor oil triisostearate, POE hydrogenated castor oil monopyroglutamate monoisostearate diester, POE hydrogenated castor oil maleic acid or any other POE castor oil hydrogenated castor oil derivative, POE sorbitan beeswax or any other POE beeswax lanolin derivative, coconut oil fatty acid diethanolamide, laurate monoethanolamide, fatty acid isopropanolamide, or any other alkanolamide, POE propylene glycol fatty acid esters, POE alkylamines, POE fatty acid amides, sucrose fatty acid esters, POE nonylphenyl formaldehyde condensation products, alkylethoxydimethylamineoxide, trioleylphosphoric acid, or any other hydrophilic nonionic surfactant, or any other surfactant.

In addition, oils may be included in the composition. Oils may act as penetrating transdermal carriers that penetrate the skin the quickly and aid in transport of other components present in the composition of the present invention. Examples of oils that may be utilized include almond oil, anise oil, apricot kernel oil, apricot oil, avocado oil, balm mint oil, basil oil, bee balm oil, bergamot, bergamot oil, birch oil, bitter almond oil, bitter orange oil, caraway oil, cardamom oil, castor oil, cedarwood oil, cinnamon oil, clay oil, clove oil, cloveleaf oil, coconut oil, fractionated coconut oil, cottonseed oil, cypress oil, eucalyptus oil, evening primrose oil, fennel oil, gardenia oil, geranium oil, ginger oil, grapefruit oil, grape seed oil, hazelnut oil, hops oil, hyptis oil, indigo bush oil, jasmine oil, jojoba oil, juniper oil, kiwi oil, kukui nut oil, laurel oil, lavender oil, lemon oil, lemongrass oil, linden oil, linseed oil, lovage oil, macadamia nut oil, maize oil, matricaria oil, musk rose oil, neroli oil, nutmeg oil, olibanum, olive oil, orange flower oil, orange oil, palm oil, patchouli oil, peach kernel oil, peanut oil, pecan oil, pennyroyal oil, peppermint oil, persic oil, pine oil, pine tar oil, poppy-seed oil, rapeseed oil, rose oil, rose hips oil, rosemary oil, rue oil, sage oil, sambucus oil, sandalwood oil, sassafras oil, sesame oil, silver fir oil, soybean oil, spearmint oil, sunflower oil, sweet almond oil, sweet marjoram oil, sweet violet oil, tar oil, tea tree oil, thyme oil, wheat germ oil, wild mint oil, yarrow oil, ylang ylang oil, walnut oil, tall oil, thistle seed oil, hydrogenated vegetable oils, or any other suitable oil.

Moreover, the composition may include extracts such as acacia extract, alfalfa extract, algae extract, aloe extract, aloe vera gel, aloe vera gel condensed, althea extract, anise extract, apple extract, apricot extract, apricot kernel oil, arnica extract, artichoke extract, asafoetida extract, avocado extract, azulene, balm mint extract, balm mint oil, banana extract, barley extract, bee pollen extract, bioflavonoids, birch leaf extract, black cohosh, black currant extract, black walnut extract, bladderwrack extract, borage extract, botanical extracts, burdock extract, burnet extract, butcher's broom extract, calendula extract, camomile extract, caper extract, carrageenan extract, carrot extract, carrot oil, centella, cherry bark extract, cinchona extract, cinquefoil extract, citroflavonoid water soluble, citrus bioflavonoid complex, clover blossom extract, coltsfoot extract, cornfrey extract, coneflower extract, cornflower extract, corn silk extract, couch grass, crataegus extract, cucumber extract, cypress extract, dandelion extract, elder flower extract, eleuterococcus, elm bark extract, licorice extract, eucalyptus extract, everlasting extract, fennel extract, fenugreek extract, fern extract, gardenia extract, garlic extract, gerrtian extract, gingko biloba extract, ginko extract, ginseng extract, glycyrrhetinic acid, glycyrrhizic acid, grape extract, grape leaf extract, grape skin extract, guarana extract, Hawaiian ginger extract, hayflower extract, helichrysum, henna extract, hesperidin complexes, hesperidin methyl chalcone, hibiscus extract, hops extract, horse chestnut extract, horsetail extract, hypericum extract, indian cress extract, ivy extract, juniper extract, kelp extract, kiwi extract, laminaria extract, lavender extract, lemon balm, lemon extract, lettuce extract, licorice extract, linden extract, madder, mallow extract, matricaria extract English, milfoil extract, mistletoe extract, mushroom extract, myrrh extract, nettle extract, oak root extract, oat extract, onion extract orange blossom extract, orange flowers extract, pansy extract, parsley extract, pellitory extract, pennyroyal extract, peppermint extract, periwinkle extract, pine needle extract, plantain extract, pollen extract, quince seed, rauwolfia extract, restharrow extract, rhatany extract, rhubarb root extract, rice bran extract, rose hips extract, rosemary extract, sage extract, sambucus extract, sanguinaria root extract, saponaria extract, sea weed extract, soy extract, soy protein, soy sterol, spearmint extract, sulfur tar complex, sunflower extract, sweet clover extract, tea extract, tea tree oil, thistle extract, thyme extract, tomato extract, tormentill extract, valerian extract, walnut extract, water cress extract, wheat bran extract, wheat germ extract, white nettle extract, white willow bark extract, wild indigo, witch hazel extract, yarrow extract, zedoary oil, ginger oil, cinnamon oil, sugar cane extract, citrus blossom extract, pineapple extract, licorice oil, olive oil, carrot seed oil, jojoba oil, wheat germ, aloe barbadensis extract, apricot extract, arnica montana extract, balm mint extract, bamboo extract, bearberry extract, beet extract, bilberry extract, birch leaf extract, blackberry leaf extract, bladderwrack extract, buckwheat extract, burdock extract, butcherbroom extract, calendula extract, carrot extract, matricaria extract, cherimoya extract, jujube extract, coltsfoot extract, cornfrey extract, coneflower extract balsam copaiba, cornflower extract, cucumber extract, dog rose hips extract, fennel extract ginger extract, ginkgo extract, ginseng extract, camellia sinensis extract, guarana extract, crataegus monogina extract, hayflower extract, henna extract, hops extract, horsetail extract, horsechestnut extract, hydrocotyl extract, ivy extract, Job's tears extract, juniperus communis extract, Karite extract, kiwi extract, lady's mantle extract, laminaria digitata extract, lavender extract, lemon peel extract, licorice extract, linden extract, lithospermum officinale extract, mallow extract, mango extract, marshmallow extract, melon extract, mimosa tenuiflora bark extract, white oak bark extract, English oak extract, oyster shell extract, pansy extract, peach extract, capsicum frutescens oleoresin, capsicum frutescens extract, peppermint extract, quillaja saponaria extract, raspberry extract, krameria triandra extract, rosemary extract, sage extract, St. John's wort extract, stinging nettle extract, strawberry extract, soapwort extract, thyme extract, walnut extract, watercress extract, wheat germ extract, willow bark extract, witch hazel extract, or any other extract.

The composition may include skin protectants such as allantoin, aloe vera gel, anise extract, avocado oil unsaponifiables, carboxymethyl chitin, chondroitin sulfate, collagen, collagen amino acids, embryo extract, glyceryl ricinoleate, hydrolyzed animal elastin, hydrolyzed milk protein, hydrolyzed vegetable protein, linoleic acid (and) linolenic acid (and) arachidonic acid, liposomes, perfluoropolymethyl-isopropyl ether, plankton extract, and spine marrow extract.

The composition may include disinfectants, antiseptics, or drug substances. Incorporation of one or more disinfectants or antiseptics is especially useful in those situations where it is important to inactivate the microorganisms which remain on the skin after normal cleansing. Incorporation of a drug substance in the composition may be useful for the prevention or treatment of various skin disorders or to deliver drug substances to the skin which are advantageously administered topically for percutaneous absorption.

Disinfectants and antiseptics may be ambazone, benzoic acid, bithionol, bromsalans, dibromsalan, metabromsalan, tribromsalan, camphor, carbolic acid, cethexonium bromide, chlorhexidine acetate, chlorhexidine gluconate solution, chloroazodin, chlorocresol, chlorothymol, chloroxylenol, clorophene, cresol, dichlordimethylhydantoin, dichlorobenzyl alcohol, dichloroxylenol, dofamium chloride, domiphen bromide, ethacridine lactate, menthol, methylbenzethonium chloride, nitromersol, noxythiolin, and triclosan. Other relevant examples are sodium pyrithione, sodium ricinoleate, thimerosal, trichlocarban, undecylenamidopropyltrimethyl ammonium methosulfate, undecylenic acid, zinc pyrithione, and zinc undecylenate, or any other disinfectant or antiseptic.

A drug substance may be any compound or mixture thereof that may produce a beneficial effect on the human to whom the drug substance has been given. Drug substances may be any physiologically or pharmacologically substance that produces a localized or systemic effect in mammals including humans. Drug substances may be anti-inflammatory compounds, analgesics, tranquilizers, cardiac glycosides, narcotic antagonists, antiparkinsonism agents, antidepressants, antineoplastic agents, immunosuppressants, antiviral agents, antibiotic agents, appetite suppressants, antiemitics, antihistamines, antimigraine agents, coronary, cerebral or peripheral vasodilators, antianginals, calcium channel blockers, hormonal agents, contraceptive agents, antithrombotic agents, antihypertensive agents, chemical dependency drugs, local anesthetics, corticosteroids, dermatological agents and the like, vitamins like vitamin A such as all-trans retinol, retinol acetate, retinol palmitate, retinol propionate, betacarotene, halibut-liver oil, shark-liver oil, vitamin $B_1$ such as thiamine hydrochloride, benfotiamine, bisbentiamine, bisbutiamine, bisibutiamine, betoiamine hydrochloride, cetotiamine hydrochloride, cocarboxylase, cycotiamine, fursultiamine, vitamin $B_2$ such as riboflavine, riboflavine tetrabutyrate, flavine adenine dinucleotide, vitamin $B_6$, vitamin $B_{12}$ such as cobalamins, $B_{12}$ TAM, cobamamide, cyanocobalamin, mecobalamin, other vitamins of the B group, vitamin C such as ascorbic acid, vitamin D such as ergocalciferol (vitamin $D_2$), cholecalciferol (vitamin $D_3$), calcifediol, calcitriol, alfacalcitriol, dihydrotachysterol, alfacalcidol, calcifediol, calcitriol, cholecalciferol, cod-liver oil, dihydrotachysterol, ergocalciferol, vitamin E, alpha tocopherols, tocopheryl nicotinate, tocopherylquinone, wheat-germ oil, vitamin K such as phytomenadione, menadiol sodium diphosphate, menadione, vitamin P, sucrose sulfate esters such as sucralfate, sucrose octasulfate and salts, esters and complexes thereof, antibacterials such as phenoxyethanol, or any other drug substance.

The composition may include analgesic compound such as aloe vera, MSM, emu oil, menthol, glucosamine, chondroitin, a capsaicinoid, arnica extract, coriander oil, Roman chamomile oil, willow bark extract, feverfew extract, St. John's wort extract, kava kava extract, nettle leaf, acetylsalicylic acid, Bala, black cohosh, black snakeroot, bugbane, squawroot, bupleurum, calendula, camphor, cayenne, devil's claw root, evening primrose oil, ginger, gotu kola, gingkgo, juniper, lavender oil, licorice, marjoram, meadow sweet, menthol, passion flower, quercetin, salicinum, wild yam, wintergreen, wood betony, wormwood, or any other analgesic.

The composition may include anti-inflammatory compounds. Anti-inflammatory compounds may be aloe vera, MSM, emu oil, chondroitin, glucosamine, a capsaicinoid, arnica extract, grape seed extract, coriander oil, marigold extract, nettle leaf extract, Roman chamomile oil, blue-bottle extract, St. John's wort, willow bark extract, witch hazel extract, feverfew extract, barley grass, black cohosh, black snakeroot, bugbane, squawroot, Boswellia, borage, bromelain, burdock, calendula, cayenne, dandelion, devil's claw root, DHEA (dehydroepiandosterone), Echinacea, elderflower, evening primrose oil, flaxseed, ginkgo, ginger, ginseng, Hawthorne, kaempferol, licorice, life root, golden Senecio, squaw weed, golden groundsel, cocash weed, coughweed, ragwort, golden ragwort, grundy swallow, linden, marjoram, meadow sweet, NDGA, neem, Padma 28, quercetin, shea butter, turmeric, wild yam, wormwood, yucca, bisabolol, sucralfate, LIPACIDE, gauaiazulene, essential fatty acids, poly-unsaturated fatty acid derivatives from plant seed oils and other vegetable sources, or any other anti-inflammatory. Essential fatty acids may include omega-3 and omega-6 fatty acids such as linolenic acid and alpha linolenic acid. In addition, any known herbs or various compounds that contain EFAs may be included in the composition. Examples of such herbs include flaxseed and evening primrose oil.

The composition may include compounds having antineuralgic effects to provide relief of pain or discomfort along a course of a nerve or in an area of distribution of the nerve. Antineuralgics may be a capsaicinoid, Roman chamomile oil, coriander oil, or any other antineuralgic compound.

The composition may include compounds having antioxidant activity to prevent damage or deterioration of tissue. Antioxidants may be chondroitin, ascorbic acid, vitamin C, cocoa butter, grape seed extract, St. John's wort extract, coriander oil, cysteine, barley grass, bilberry, Echinacea, garlic, ginger, ginkgo, ginseng, grape seed proanthocyanidin extract, green tea, Hawthorne, lemon balm, milk thistle, oregano, peppermint, pomegranate juice, purslane, pycnogenol, red wine, rosemary, schizandra, wuweizi, wurenchun, trilinolein, sanchi, tartaric acid, turmeric, α-tocopherol or any other tocopherol, dibutylhydroxytoluene butylhydroxyanisole, or any other antioxidant.

The composition may include a blood circulation promoter to provide increased blood circulation to an area to which the composition is applied. Blood circulation promoters may be MSM (methylsulfonylmethane), arnica extract, Roman chamomile oil, nettle extract, marigold extract, grape seed extract, blue-bottle extract, coriander oil, lime tree extract, marigold extract, feverfew extract, St. John's wort extract, witch hazel extract, arjuna, Bala, benzoin, bilberry, black pepper, blue gum eucalyptus, blue vervain, borneol, butcher's broom, cayenne, cypress, geranium, ginger, ginkgo, grape seed proanthocyanidin extract, Hawthorne, L-arginine, lemon, lemon grass, linden flowers, niaouli, oat straw, orange blossom, passion flower, Peru balsam, pine, prickly ash bark, rose oils, rosemary, Spanish sage, spruce, Tien Chi ginseng, thyme, violet, white birch, yohimbe, or any other blood circulation promoter.

The composition may include an effective amount of at least one compound having antidepressant, anti-anxiety, or anti-stress activity. Antidepressant, anti-anxiety, or anti-stress compounds may be MSM (methylsulfonylmethane), kava kava extract, Roman chamomile extract, feverfew extract, St. John's wort extract, bee pollen, bergamot, black cohosh, black horehound, bugleweed, California poppy, clary sage, cowslip, damiana, DHEA (dehydroepiandrosterone), geranium, ginseng, gotu kola, grapefruit, hyssop, Jamaican dogwood, lady's slipper, lavender, lemon balm, licorice, linden, lobelia, mate, mistletoe, motherwort, mugwort, oat straw, passion flower, peppermint, rosemary, skullcap, valerian root, vervain, wild lettuce, wood betony, or any other antidepressant, anti-anxiety, or anti-stress compound.

The composition may comprise any pain relieving, anti-inflammatory, antioxidant, blood circulation promoter, antidepressant, anti-anxiety, or anti-stress type of herb. Such herbs may be arjuna, Bala, barley grass, bee pollen, benzoin, bergamot, bilberry, black cohosh, black horehound, black pepper, blue gum eucalyptus, blue vervain, borage, borneol, Boswellia, bromelain, bugleweed, bupleurem, burdock, butcher's broom, California poppy, camphor, cayenne, clary sage, cocash weed, cowslip, coughweed, cypress, damiana, dandelion, devil's claw root, DHEA (dehydroepiandosterone), echinacea, elderflower, evening primrose oil, flaxseed, garlic, geranium, ginger, ginkgo, ginseng, golden groundsel, golden ragwort, golden Senecio, gotu kola, grapefruit, grape seed proanthocyanidin extract, green tea, grundy swallow, Hawthorne, heather, hyssop, Jamaican dogwood, juniper, kaempferol, L-arginine, lady's slipper, lavender, lemon, lemon balm, lemon grass, licorice, life root, linden, lobelia, marjoram, mate, meadow sweet, milk thistle, mistletoe, motherwort, mugwort, NDGA (nordihydroguaiaretic acid), neem, niaouli, oat straw, orange blossom, oregano, Padma 28, passion flower, peppermint, Peru balsam, pine, pomegranate juice, prickly ash bark, purslane, pycnogenol, quercetin, ragwort, red wine, rose oils, rosemary, salicinum, schizandra, sharp sorrel, skullcap, Spanish sage, spruce, squaw weed, Tien Chi ginseng, thyme, trilinolein, turmeric, valerian root, vervain, violet, white birch, wild lettuce, wild yam, wintergreen, wood betony, wormwood, yohimbe, yucca, or any other pain relieving, anti-inflammatory, antioxidant, blood circulation promoting, anti-depressant, anti-anxiety, or anti-stress type of herb.

Further, the composition may include extracts having various medicinal effects. Such extracts may be aloe extract, candock extract, carrot extract, cinchona extract, clove extract, common fennel extract, cornflower extract, creeping saxifrage extract, cucumber extract, dishcloth gourd extract, eucalyptus extract, field horsetail extract, hamamelis extract, herbaceous peony extract, horse chestnut extract, Houttuynia cordate extract, iris rhizome extract, lemon extract, licorice root extract, Lithospermum erythrorhizon extract, melilot extract, melissa extract, mulberry extract, peach extract, peach leaf extract, Phellon dendron amurense Rupr extract, placenta extract, primrose extract, raspberry extract, rose extract, Rehmannia glutinosa extract, sage extract, seaweed extract, silk extract, soapwort extract, Sophora angustifolia extract, tea extract, thyme extract, thymus extract, white dead nettle extract, or any other medicinal extract.

The drug and medicinal ingredients that may be included in the composition are not limited by the above-mentioned ingredients. Drug and medicinal ingredients may be formulated alone into the composition or two or more types of medicinal ingredients may be combined and formulated suitably depending upon the objective. Further, drug and medicinal ingredients may not only be used in a free form, but may also be formulated into the composition in the form of a salt of an acid or base when capable of forming a salt or in the form of an ester when having a carboxylic acid group.

The composition may contain sunscreen. Sunscreen may be allantoin, PABA, p-aminobenzoates, benzophenone-2, benzophenone-6, benzoresorcinol, benzyl salicylate, cinoxate, dioxybenzone, esculoside, ethyl 4-bis(hydroxypropyl) aminobenzoate, ethylhexyl p-methoxycinnamate, etocrylen, glyceryl aminobenzoate, homosalate, methyl salicylate, methyl anthranilate, methyl eugenol, 3-(4-methylbenzylidene)boran-2-one, mexenoe, octabenxone, octocrylene, oxybenzone, padimate, 2-phenyl-1H-benzimidazole-5-sulphonic acid, sulisobenzone, 3-benzylidene camphor, coffee extract, ethyl salicylate, glyceryl PABA, homosalate, isopropylbenzylsalicylate, menthyl anthranilate, nylon-12 (and) titanium dioxide, octyl dimethyl PABA, octyl methoxycinnamate, octyl salicylate, octyl triazone, orizanol, PEG-25 PABA, TEA-salicylate, titanium dioxide, zinc oxide, benzophenone-1, benzophenone-3, benzophenone-4, bensophenone-8, benzophenone-9, benzophenone-11, benzophenone-12, butyl methoxydibenzoylmethane, 4-isopropyl dibenzoyl methane, avocadin, argana oil, DEA-methoxycinnamate, drometrizole, ethyl dihydroxypropyl p-aminobenzoic acid, etocrylene, isopropyl methoxycinnamate, 3-(4-methylbenzylidene)-camphor, octocrylene, octrizole, octyl dimethyl PABA, octyl methoxycinnamate, octyl salicylate, octyl triazone, PABA, shea butter, TEA-salicylate, tri-PABA-panthenol, or any other sunscreen.

The composition may include insect repellent. Insect repellent may be butopyronoxyl, butylethylpropanediol, dibutyl phthalate, diethyltoluamide, dimethyl phthalate, ethohexadiol, citronella, camphor, or any other insect repellant.

The composition may include preservatives. Preservatives may be grape seed extract, cocoa butter, methylparaben, propylparaben, diazolindinyl urea, sorbic acid, phenoxyethanol, ethylparaben, butylparaben, sodium butylparaben, or any other preservative. The composition may or may not include a preservative, and may include a plurality of preservatives. Preservatives may help to prevent bacteria and fungus from developing in the composition. Preservatives may also increase the shelf life of the composition. Shelf life may refer to the time between when the composition is produced and the time the composition is applied to a skin surface. Preservatives may serve different purposes which are known to those having skill in the art. One embodiment of the composition includes Dehydroacetic Acid as a preservative. The composition may include from 0% to 0.1% Dehydroacetic Acid. Another embodiment of the composition may include Caprylyl Glycol as a preservative. The composition may include from 0% to 1.5% Caprylyl Glycol. The preservatives used in the composition should not be limited to Dehydroacetic Acid and Caprylyl Glycol; other preservatives known to those having skill in the art may be used.

The composition may also include sugar, or a sugar equivalent, or other exfoliants or granular materials which assist in exfoliation such as pumus, apricot meal, ground oats, walnut shell flour, and ground almond meal. One embodiment of the composition includes white sugar. White sugar its equivalent may make up from 15% to 25% of the entire composition. The addition of white sugar or its equivalent in the composition may be used as a scrub mixture to be applied to the skin surface. The sugar may be stirred with the composition to make the scrub mixture.

The composition may include a suitable fragrance or color to an extent not impairing the desired effect of the present invention. The composition may include fragrance. Any type of natural or synthetic fragrance, such as floral, herbal or fruity fragrance could be utilized. The use of fragrance is well known in the cosmetic art and in the art of over-the-counter drug formulation, and many suitable fragrances are known in the art. The stability and function of the composition is not altered by the presence or absence of fragrance. Freesia essential oil may be used as a natural fragrance. Other essential oils may also be used as a natural fragrance. Fragrance can be omitted, and it may be desirable to omit fragrance in circumstances in which the composition is intended for use on sensitive individuals or individuals who may undergo an allergic reaction to fragrance. The composition may include a colorant. Any type of natural or FD&C colorant, such as FD&C Blue No. 1, may be utilized. Alternatively, the composition may be colorless, or possess a color provided by one or more of the compounds present therein.

The composition may include various pharmaceutically or cosmetically acceptable excipients or additives such as those which usually are employed in cosmetic or pharmaceutical compositions. Excipients or additives may be pH adjusting agents, stabilizing agents, coloring agents, foaming agents, viscosity adjusting agents, skin lightening agents such as arbutin, thickening agents such as alginate and Carbomer-940, spreading agents, pearl gloss agents, agents which protect the skin against aggressive substances in water, atmospheric air and on solid surfaces such as salts, pigments, fats, and esters, protecting agents such as chitosan, salts, waxes, and long chain alcohols. Other relevant additives include lactic acid, citric acid, glycolic acid, succinic acid, tartaric acid, dl-malic acid, potassium carbonate, sodium hydrogencarbonate, ammonium hydrogencarbonate, and other pH adjusters.

The composition may be used in the form of a pharmaceutical, quasi-pharmaceutical, or cosmetic. It may take the form of a lotion, cream, ointment, powder, gel, aerosol, foam, facial cleanser, balm, gel, shampoo, conditioner, wash, rinse, towelette, beauty liquid, pack, mask, makeup, foundation, scrub, exfoliant, soap, lipstick, hair cosmetic, body cosmetic, or any other suitable form for application to external surfaces of the body. The form capable of being taken by the composition is not limited to these forms however.

In an embodiment of the composition, various natural ingredients may be included such as aloe vera gel, almond oil, avocado oil, coconut oil, emu oil, freesia essential oil, olive oil, royal jelly, sesame oil, vegetable glycerin, vitamin E, and witch hazel extract. For example, these ingredients may be combined in the following way: aloe vera gel 33% by volume, almond oil 4% by volume, avocado oil 11% by volume, coconut oil 2% by volume, emu oil 2% by volume, freesia essential oil 0.1% by volume, olive oil 6% by volume, royal jelly 0.2% by volume, sesame oil 8% by volume, vegetable glycerin 0.5% by volume, vitamin E 0.2% by volume, and witch hazel extract 33% by volume.

Aloe vera gel soothes the skin and contains properties that promote removal of dead skin cells and promotes the body's normal growth of living cells. With anti-inflammatory properties, it improves the body's healing capacities. It also leaves a protective coating on the skin. Aloe vera gel is the inner gel from the leaves of the aloe plant.

Aloe may reduce inflammation, decreases swelling and redness, and accelerates wound healing. Aloe may also aid in keeping the skin supple. Aloe's healing power may come from increasing the availability of oxygen to the skin, and by increasing the synthesis and strength of tissue.

Almond oil has emollient and moisturizing properties that soothe, soften, and recondition skin. It contains minerals, vitamins, and protein for the skin.

Avocado oil has moisturizing properties. It penetrates the skin, is beneficial to healing processes, and protects the skin from UV rays.

Coconut oil has moisturizing, anti-microbial, anti-bacterial, and anti-fungal properties.

Emu oil has a natural anti-inflammatory agent, is non-irritating to the skin, and is highly penetrating. It acts as a carrying agent for other ingredients. It heightens the body's scar healing abilities. It is moisturizing and lightens the appearance of redness in the skin.

Emu oil may be obtained from a subcutaneous layer of fat found just under the skin on the back of an emu, a large, flightless Australian bird which is related to and resembles the ostrich. Emu oil exhibits certain surface penetrating characteristics that, when the oil is combined with other compounds, increases the penetration of the compound as a whole.

Freesia essential oil has a pleasant scent and is used in aroma therapy. In this embodiment it is used as a fragrance.

Olive oil has emollient and antioxidant properties. It may be a carrier oil since it penetrates the skin.

Royal jelly is a nutritious substance secreted by the pharyngeal glands of worker bees that serves as food for all young larvae and as the only food for larvae that will develop into queen bees. It has anti-inflammatory properties and contains proteins, lipids, vitamins, and enzymes that aid in healing wounds. As used in this embodiment, royal jelly is freeze-dried and powdered in a 3.5× concentration.

Sesame oil has emollient, anti-inflammatory, and UV protection properties. It is also readily absorbed into the skin.

Vegetable glycerin has humectant, emollient, emulsifier, preservative, and lubricant properties.

Vitamin E oil has antioxidant, anti-inflammatory, analgesic, and preservative properties.

Witch hazel extract comes from the hamamelis virginiana tree or shrub. It has astringent, anti-inflammatory, and anti-oxidant properties. In this embodiment, witch hazel extract comprises about 86% witch hazel and about 14% alcohol.

A method of treating scars or rosacea is now described. One methodological step may include providing a scar or rosacea treatment composition. The composition may include almond oil, aloe, avocado oil, coconut oil, emu oil, glycerin, royal jelly, sesame oil, vitamin E, and witch hazel. The composition may also comprise the ingredients listed in Examples 1-7, discussed infra, and combinations thereof. An additional methodological step may include supplying a skin surface having a scar. Yet another methodological step may include applying a scar or rosacea composition to a scar. Moreover, another methodological step may include applying a scar or rosacea composition to unscarred areas of a skin surface.

The following are exemplary embodiments of combinations and mixtures of the ingredients discussed in detail above that may be used as working examples of the present composition. In no way should the present composition and method be limited to the examples listed below.

EXAMPLES

Example 1

Method of Preparation

One embodiment of Example 1 composition may be prepared in the following manner. Using room temperature ingredients, combine Aloe Vera gel, Witch Hazel, Glycerin, Royal Jelly powder and Vitamin E Oil. Using a medium beater speed, blend ingredients for approximately three minutes. Heat the Coconut oil just until it is pouring consistency. To the Coconut oil, add Sesame oil, Avocado oil, Olive oil, Almond oil, Coconut oil Emu oil and essential oil and mix to combine. With mixer running, slowly add the oil mixture to the Aloe Vera mixture. Continue blending for three minutes until thoroughly combined. Pour into containers and seal.

Method of Use

One embodiment of Example 1 composition may be used in the following manner. Example 1 composition may be applied in the morning and evening. Massage in using upward strokes. Example 1 composition may act as a complete toner and moisturizer formulated for mature skin. It may be readily absorbed, and may provide maximum nourishment and moisturizing.

Example 1

1 c. aloe vera (0-3 c.)
1 c. witch hazel (0-3 c.)
1 tsp. glycerin (1-2 Tbsp)
½ tsp. freeze dried royal jelly (0-1 Tbsp.)

½ tsp. Vitamin E oil (0-1 Tbsp.)
¼ c. Kukui Nut oil (0-¾ c.)
⅓ c. Avocado oil (0-¾ c.)
3 Tbsp. Olive oil (0-½ c.)
2 Tbsp. Almond oil (0-½ c.)
1 Tbsp. coconut oil (0-½ c.)
1 Tbsp. Emu oil (0-½ c.)
⅛ tsp. Freesia essential oil (0-½ tsp.)

Example 2

Method of Preparation

One embodiment of Example 2 composition may be prepared in the following manner. Using room temperature ingredients, combine Aloe Vera gel, Witch Hazel, Glycerin, Royal Jelly powder and Vitamin E Oil. Using a medium beater speed, blend ingredients for approximately three minutes. Heat the Coconut oil just until it is pouring consistency. To the Coconut oil, add Sesame oil, Avocado oil, Olive oil, Almond oil, Coconut oil Emu oil and essential oil and mix to combine. With mixer running, slowly add the oil mixture to the Aloe Vera mixture. Continue blending for three minutes until thoroughly combined. Pour into containers and seal.

Method of Use

One embodiment of Example 2 composition may be used in the following manner. Example 2 composition may be applied twice daily, morning and evening. Massage into face and neck using upward strokes. The appearance of redness may improve in approximately four months. Continuing treatment may help to control symptoms.

Example 2

1 c. aloe vera (0-3 c.)
1 c. witch hazel (0-3 c.)
1 tsp. glycerin (1-2 Tbsp)
½ tsp. freeze dried royal jelly (0-1 Tbsp.)
½ tsp. Vitamin E oil (0-1 Tbsp.)
¼ c. Sesame oil (0-¾ c.)
¼ c. Avocado oil (0-¾ c.)
2 Tbsp. Olive oil (0-½ c.)
2 Tbsp. Almond oil (0-½ c.)
2 Tbsp. Coconut oil (0-½ c.)
2 Tbsp. Emu oil (0-½ c.)
⅛ tsp. Freesia essential oil (0-½ tsp.)

Example 3

Method of Preparation

One embodiment of Example 3 composition may be prepared in the following manner. Using room temperature ingredients, combine Aloe Vera gel, Witch Hazel, Glycerin, Royal Jelly powder and Vitamin E Oil. Using a medium beater speed, blend ingredients for approximately three minutes. Heat the Coconut oil just until it is pouring consistency. To the Coconut oil, add Sesame oil, Avocado oil, Olive oil, Almond oil, Coconut oil Emu oil and essential oil and mix to combine. With mixer running, slowly add the oil mixture to the Aloe Vera mixture. Continue blending for three minutes until thoroughly combined. Pour into containers and seal.

Method of Use

One embodiment of Example 3 composition may be used in the following manner. Example 3 composition may be applied twice daily, morning and evening. After cleansing face, massage a small amount of the composition into the skin. You will not need an additional toner when using Example 3 composition.

Example 3

1 c. aloe vera (0-3 c.)
1¾ c. witch hazel (0-3 c.)
1 tsp. glycerin (0-2 Tbsp.)
½ tsp. freeze dried royal jelly (0-1 Tbsp.)
½ tsp. Vitamin E oil (0-1 Tbsp.)
¼ c. Sesame oil (0-¾ c.)
⅓ c. Hazelnut oil (0-¾ c.)
3 Tbsp. jojoba oil (0-½ c.)
2 Tbsp. Almond oil (0-½ c.)
1 Tbsp. Coconut oil (0-½ c.)
2 Tbsp. Emu oil (0-½ c.)
⅛ tsp. freesia essential oil (0-½ tsp.)

Example 4

Method of Preparation

One embodiment of Example 4 may be prepared in the following manner. Using room temperature ingredients combine the Sesame oil, Avocado do oil, Olive oil, Almond oil, and Emu oil. Heat the Coconut oil just until it's of pouring consistency. Add the Coconut oil to the mixture of other oils. Combine jojoba beads or oil, beeswax and shea butter. Using moderate heat, heat just until completely melted. Add the Naturella oil mixture. When slightly cooled but still liquid, add the essential oil. Stir well and pour into containers. Cool completely.

Method of Use

One embodiment of Example 4 composition may be used in the following manner. Example 4 composition may be a deep penetrating cream formulated for very dry skin. It may be used in areas of the body that need additional moisturizing such as cuticles, hands, feet, knees, or elbows.

Example 4

5 Tbsp. Sesame oil (0-¾ c.)
4 Tbsp. Avocado oil (0-¾ c.)
3 Tbsp. Olive oil (0-¾ c.)
2 Tbsp. Almond oil (0-¾ c.)
1 Tbsp. Coconut oil (0-¾ c.)
1 Tbsp. Emu oil (0-¾ c.)
⅛ tsp. freesia essential oil (0-½ tsp.)
1 tsp. jojoba oil or beads (0-2 Tbsp.)
2½ oz. beeswax beads or grated beeswax (0-4 oz.)
4 oz. shea butter (0-5 oz.)

Example 5

Method of Preparation

One embodiment of Example 5 composition may be prepared in the following manner. Using room temperature ingredients, combine Aloe Vera gel, Witch Hazel, Glycerin, Royal Jelly powder and Vitamin E Oil. Using a medium beater speed, blend ingredients for approximately three minutes. Heat the Coconut oil just until it is pouring consistency. To the Coconut oil, add Sesame oil, Avocado oil, Olive oil, Almond oil, Coconut oil Emu oil and essential oil and mix to combine. With mixer running, slowly add the oil mixture to the Aloe Vera mixture. Continue blending for three minutes until thoroughly combined. Pour into containers and seal.

Method of Use

One embodiment of Example 5 may be used in the following manner. Example 5 composition may be applied twice daily, morning and night. Massage it in well, using a slow, deep movement. Massaging a scar may help it heal. Improvement may be noticed within two weeks. The scar may continue to lighten and flatten out for approximately six months. Treatment may be stopped once maximum results are achieved.

Example 5 aloe vera gel 33% by volume
almond oil 4% by volume
avocado oil 11% by volume
sesame oil 8% by volume
coconut oil 2% by volume
emu oil 2% by volume
olive oil 6% by volume
royal jelly 0.2% by volume
witch hazel extract 33% by volume
vegetable glycerin 0.5% by volume
vitamin E 0.2% by volume

Example 6

Method of Preparation

One embodiment of Example 6 composition may be prepared in the following manner. Using room temperature ingredients, combine Aloe Vera gel, Witch Hazel, Glycerin, Royal Jelly powder and Vitamin E Oil. Using a medium beater speed, blend ingredients for approximately three minutes. Heat the Coconut oil just until it is pouring consistency. To the Coconut oil, add Sesame oil, Avocado oil, Olive oil, Almond oil, Coconut oil Emu oil and essential oil and mix to combine. With mixer running, slowly add the oil mixture to the Aloe Vera mixture. Continue blending for three minutes until thoroughly combined. Pour into containers and seal.

Method of Use

One embodiment of Example 6 may be used in the following manner. Example 6 composition may be applied in the morning or evening. Massage in using upward strokes. Example 6 may be a complete toner and moisturizer. Example 6 may be applied to correct the pH balance of skin and moisturize skin.

Example 6 aloe vera gel 33% by volume
almond oil 4% by volume
avocado oil 11% by volume
coconut oil 2% by volume
emu oil 2% by volume
olive oil 6% by volume
sesame oil 8% by volume
vegetable glycerin 0.5% by volume
vitamin E 0.2% by volume
witch hazel extract 33% by volume
freesia essential oil 0.1% by volume
royal jelly 0.2% by volume

Example 7

Method of Preparation

One embodiment of Example 7 composition may be prepared in the following manner. Using room temperature ingredients, combine Aloe Vera gel, Witch Hazel, Glycerin, Royal Jelly powder and Vitamin E Oil. Using a medium beater speed, blend ingredients for approximately three minutes. Heat the Coconut oil just until it is pouring consistency. To the Coconut oil, add Sesame oil, Avocado oil, Olive oil, Almond oil, Coconut oil Emu oil and essential oil and mix to combine. With mixer running, slowly add the oil mixture to the Aloe Vera mixture. Continue blending for three minutes until thoroughly combined. Pour into containers and seal.

Method of Use

One embodiment of Example 7 may be used in the following manner. Example 7 may be applied in the morning. Massage in using upward strokes. Example 7 may be a complete toner, moisturizer and sunscreen. Example 7 may be applied to correct the pH balance of skin, moisturize skin and protect it from harmful UVB/UVA rays throughout the day.

Example 7 aloe vera gel 33% by volume
almond oil 4% by volume
avocado oil 11% by volume
coconut oil 2% by volume
emu oil 2% by volume
freesia essential oil 0.1% by volume
olive oil 6% by volume
royal jelly 0.2% by volume
sesame oil 8% by volume
vegetable glycerin 0.5% by volume
vitamin E 0.2% by volume
witch hazel extract 33% by volume
1½ tsp/titanium dioxide (0-½ tsp.)

While this invention has been described in conjunction with the specific embodiments outlined above, it is evident that many alternatives, modifications and variations will be apparent to those skilled in the art. Accordingly, the embodiments of the invention as set forth above are intended to be illustrative, not limiting. Various changes may be made without departing from the spirit and scope of the invention as defined in the following claims.

What is claimed is:
1. A composition comprising:
a first portion for skin toning, the first portion including only:
aloe vera gel, vegetable glycerin, royal jelly freeze dried in a 3.5X concentration, vitamin E, and witch hazel extract,
wherein the first portion is prepared at a room temperature; and
a second portion for skin moisturizing, the second portion including:
coconut oil heated to a pourable consistency, almond oil, avocado oil,
emu oil, and sesame oil,
wherein the first portion and the second portion are combined in an appropriate ratio to form a combined composition, the combined composition including:
aloe vera gel present in a range of between 25% to about 40% by volume, vegetable glycerin present up to about 3% by volume, royal jelly freeze dried in a 3.5X concentration present up to about 1% by volume, vitamin E present up to 3% by volume, witch hazel extract present in a range of between 25% to about 40% by volume, coconut oil present up to about 5%, almond oil present up to about 8%, avocado oil, present in a range between about 5% and about 15%, emu oil present up to about 5% by volume, and sesame oil present in a range between about 5% and about 15%;
wherein the combined composition is blended until the combination is thoroughly blended;

wherein the combined combination reduces redness and raised features of scar tissue when applying to a skin surface.

2. The composition of claim 1, wherein the skin moisturizer contains vitamins, hydroxy acids, and retinoids.

3. The composition of claim 1, wherein the composition further contains an antineuralgic compound to produce an antineuralgic effect.

4. The composition of claim 1, wherein the composition further comprises antioxidants.

5. The composition of claim 1, wherein the composition further includes an effective amount of at least one compound having antidepressant, anti-anxiety, or anti-stress activity.

6. The composition of claim 5, wherein the effective amount of at least one compound having antidepressant, anti-anxiety, or anti-stress activity is an herb.

7. The composition of claim 1, wherein the skin moisturizer exhibits occlusive properties.

8. The composition of claim 1, wherein the second portion exhibits non-occlusive properties.

9. The composition of claim 1, wherein the composition further contains a sunscreen.

10. The composition of claim 1, wherein the composition further contains consists of an insect repellant.

11. The composition of claim 1, wherein the composition further contains consists of a fragrance.

12. The composition of claim 11, wherein the fragrance is an essential oil.

13. The composition of claim 1, wherein the composition is odorless.

14. The composition of claim 1, wherein the composition includes a colorant.

15. The composition of claim 1, wherein the composition is colorless.

16. The composition of claim 1, wherein the composition further includes excipients.

17. The composition of claim 1, wherein the composition further includes consists of a preservative.

18. The composition of claim 1, wherein a sugar comprises 15% to 25% of the composition.

19. A method for reducing redness and scars and the a treatment of rosacea comprising:
preparing a first portion of a combined composition at a room temperature, the first portion including only: aloe vera gel, vegetable glycerin, royal jelly freeze dried in a 3.5X concentration, vitamin E, and witch hazel extract;
preparing a second portion of the combined composition, the second portion including:
coconut oil heated to a pourable consistency, almond oil, avocado oil, emu oil, and sesame oil;
combining the first portion and the second portion at an appropriate ration to form the combined composition, the combined composition including: aloe vera gel present in a range of between 25% to about 40% by volume, vegetable glycerin present up to about 3% by volume, royal jelly freeze dried in a 3.5X concentration present up to about 1% by volume, vitamin E present up to 3% by volume, witch hazel extract present in a range of between 25% to about 40% by volume, coconut oil present up to about 5%, almond oil present up to about 8%, avocado oil present in a range between about 5% and about 15%, emu oil present up to about 5% by volume, and sesame oil present in a range between about 5% and about 15%;
blending the combined composition for approximately until thoroughly blended together; and
applying the combined composition to a skin surface to reduce redness and raised features of scar tissue.

* * * * *

UNITED STATES PATENT AND TRADEMARK OFFICE
CERTIFICATE OF CORRECTION

| | | |
|---|---|---|
| PATENT NO. | : 8,623,335 B2 | Page 1 of 1 |
| APPLICATION NO. | : 12/206833 | |
| DATED | : January 7, 2014 | |
| INVENTOR(S) | : Tauna Ann Waddington | |

It is certified that error appears in the above-identified patent and that said Letters Patent is hereby corrected as shown below:

In the Claims:

<u>COLUMN 20</u>

Claim 19, Line 7 delete "the"

Signed and Sealed this
Twenty-ninth Day of April, 2014

Michelle K. Lee
*Deputy Director of the United States Patent and Trademark Office*